(12) United States Patent
Chen

(10) Patent No.: US 9,155,510 B2
(45) Date of Patent: Oct. 13, 2015

(54) SYSTEMS AND METHODS FOR GENERATING X-RAY PHASE CONTRAST IMAGES USING A CONVENTIONAL X-RAY IMAGING SYSTEM

(71) Applicant: Wisconsin Alumni Research Foundation, Madison, WI (US)

(72) Inventor: Guang-Hong Chen, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 207 days.

(21) Appl. No.: 14/052,722

(22) Filed: Oct. 12, 2013

(65) Prior Publication Data

US 2015/0103970 A1   Apr. 16, 2015

(51) Int. Cl.
| | |
|---|---|
| *A61B 6/03* | (2006.01) |
| *G01J 9/00* | (2006.01) |
| *G01N 23/087* | (2006.01) |
| *G06T 11/00* | (2006.01) |
| *A61B 6/00* | (2006.01) |
| *G01N 23/04* | (2006.01) |
| *G01N 23/20* | (2006.01) |

(52) U.S. Cl.
CPC .............. *A61B 6/484* (2013.01); *A61B 6/582* (2013.01); *A61B 6/03* (2013.01); *A61B 6/032* (2013.01); *A61B 6/4405* (2013.01); *A61B 6/4441* (2013.01); *A61B 6/482* (2013.01); *A61B 6/5205* (2013.01); *A61B 6/583* (2013.01); *G01J 9/00* (2013.01); *G01N 23/046* (2013.01); *G01N 23/087* (2013.01); *G01N 23/20083* (2013.01); *G06T 11/005* (2013.01)

(58) Field of Classification Search
CPC .............. A61B 6/00; A61B 6/02; A61B 6/03; A61B 6/48; A61B 6/484; A61B 6/488; A61B 6/58; A61B 6/582; A61B 6/583; G09B 23/28; G01J 9/00; G01J 9/02; G01J 9/04; G01N 23/00; G01N 23/02; G01N 23/04; G01N 23/046; G01N 23/06; G01N 23/08; G01N 23/083; G01N 23/087; G01N 23/20066; G01N 23/20083; G06T 7/0012; G06T 7/0014; G06T 11/003; G06T 11/005; G06K 9/62; G06K 9/6201; G06K 9/6202; G06K 9/6203
USPC .............. 378/4, 18, 51, 53, 54, 56, 62, 91, 98, 378/98.2, 98.8, 98.12, 162, 204, 207, 210, 378/901; 382/128, 130, 131, 181, 190, 191, 382/276, 325

See application file for complete search history.

(56) References Cited

U.S. PATENT DOCUMENTS

| | | | |
|---|---|---|---|
| 2012/0128126 A1* | 5/2012 | Ishii | 378/62 |
| 2014/0185896 A1* | 7/2014 | Baturin et al. | 382/131 |
| 2014/0355740 A1* | 12/2014 | Koehiler et al. | 378/62 |

OTHER PUBLICATIONS

Kronig, On the Theory of Dispersion of X-Rays, Journal of the Optical Society of America, 1926, 12(6):547-557.

* cited by examiner

*Primary Examiner* — Anastasia Midkiff
(74) *Attorney, Agent, or Firm* — Quarles & Brady, LLP

(57) ABSTRACT

Described here are systems and methods for generating x-ray phase contrast images from conventional x-ray attenuation data. X-ray attenuation coefficients generated over a range of x-ray energies are used to compute the x-ray phase signal up to a calibration constant. This calibration constant is computed from provided calibration data, which may be obtained using a dedicated x-ray differential phase contrast imaging system to measure the decrement of the refractive index of a calibration phantom.

18 Claims, 4 Drawing Sheets

SYSTEMS AND METHODS FOR GENERATING X-RAY PHASE CONTRAST IMAGES USING A CONVENTIONAL X-RAY IMAGING SYSTEM

STATEMENT REGARDING FEDERALLY SPONSORED RESEARCH

This invention was made with government support under EB009699 and CA169331 awarded by the National Institutes of Health. The government has certain rights in the invention.

CROSS-REFERENCE TO RELATED APPLICATIONS

N/A

BACKGROUND OF THE INVENTION

The field of the invention is systems and method for x-ray imaging. More particularly, the invention relates to systems and method for generating x-ray phase contrast images from x-ray attenuation data.

X-rays have been widely used in medical imaging since their discovery in 1895. These relatively energetic photons interact with tissues that have different attenuating properties to generate contrast for visualization of the difference between tissues. Microscopically, the interaction between x-ray photons and tissue is described by different cross-sections of physical processes such as photoelectric, Compton scattering, and others. In the diagnostic x-ray energy range (10 keV-150 keV), the photoelectric effect is predominant for contrast resolution, while the other physical processes only contribute to degrade image quality. The relative contrast between two tissue types drops quickly with increases in x-ray beam energy. However, when the x-ray beam energy is too low, the deposition of x-ray energy in tissues increases, and harmful radiobiological effects may occur. Thus, a delicate balance between the contrast needed for medical diagnosis and the potential detrimental effects of x-ray deposition must be achieved for x-ray-based medical imaging.

To improve contrast resolution such that the local difference between two neighboring local regions of tissues could be better differentiated in medical diagnosis, x-ray computed tomography ("CT") was introduced in the 1970s. In this method, projection information is acquired from many different view angles and the local distribution of the x-ray attenuation coefficients is reconstructed from the acquired projection data. The introduction of CT methods significantly enhanced physicians' capabilities in medical diagnosis. However, similarly to the conventional x-ray projection method, the requirement of lowering radiation dose favors to use higher energy beams, but at the cost of a decrease in contrast resolution. In addition to the balance between contrast resolution and radiation dose, when high spatial resolution is needed for visualization of fine structures, the noise level of both x-ray projection and CT imaging increases dramatically. In order to maintain the required contrast-to-noise ratio ("CNR") for visualization of differences between tissues, a high radiation dose is required to compensate for the increase in noise level.

Since its conception, x-ray imaging has been successfully used in medical diagnosis, but the sole contrast mechanism, x-ray absorption, significantly limits wider and safer applications. An ongoing goal in the use of x-rays in medical applications is to have the lowest possible radiation dose, while maintaining the highest possible spatial and contrast resolution, in addition to having quantitative imaging capabilities.

The limitation of a single contrast mechanism in x-ray imaging has motivated investigators to explore the possibility of multiple contrast mechanisms. As a result of wave-particle duality, x-ray beams can also be viewed as waves. The only difference from the familiar wave examples is that the x-ray wavelength is very short, often on the order of angstroms. Due to their wave nature, x-rays will not only be attenuated when they penetrate through matter, but will also experience distortions in wave-front due to the interaction of the wave with the particles inside of the medium. As a result, a local phase shift will be generated in the x-ray wave after exiting the object. Physically, local phase shifts of x-ray waves are determined by the distribution of local electron density in the object. Namely, when x-rays propagate through matter, the internal structural information of the material is encoded into the corresponding wave-front distortions. Thus, by detecting the wave-front distortion in x-ray waves, one may potentially obtain the structural information of an object. Several methods have been used to extract wave front distortion; these methods are collectively referred to as x-ray phase contrast imaging methods.

Currently, the majority of investigations are still limited to the use of x-ray synchrotron radiations. The experimental results from the synchrotron facilities provide very important insights into two aspects. The first is an understanding of x-ray phase contrast signatures of specific diseased tissues for use in medical diagnosis. The second is the use of nearly ideal coherent x-ray beams to determine relevant physical parameters for future medical devices which would use conventional x-ray tubes. However, to make x-ray phase contrast imaging practical in routine medical practice, the following issues must be addressed.

First, independent of the contrast mechanism used in imaging, x-ray photons must be sufficiently energetic to be able to penetrate through the image object. In preclinical applications, such as tissue specimen imaging, photon energies can be as low as 10 keV for acceptable signal level at the detector plane. However, when a more attenuating object is imaged, such as an entire organ or portion of the human body, the low energy photons will be entirely absorbed. Therefore, it is important to extend the preclinical experimental conditions to higher energy x-ray photons. Ideally, the mean x-ray energy should be on the order of 50 keV for most human clinical applications. In addition to photon energy, it is also important that there is sufficient photon flux in order to achieve the required signal-to-noise ratio ("SNR") at the detector. Therefore, any potentially useful phase contrast imaging method should use a conventional diagnostic x-ray tube and realistically-sized image objects to further demonstrate the clinical relevance of each proposed phase sensitive imaging method.

Second, currently, for physical phantom or tissue specimen experiments, x-ray radiation dose is not a major concern. One can always increase the x-ray exposure level to increase the SNR to demonstrate feasibility of a given phase contrast imaging scheme. However, in clinical applications, the feasibility of achieving acceptable SNR at a clinically acceptable radiation dose level needs to be demonstrated.

Third, currently, due to limited x-ray source capacity when using conventional x-ray tube sources, the data acquisition time has been prolonged significantly to boost the SNR. While this may be acceptable in preclinical experiments, for routine clinical applications, data acquisition must take within seconds or even sub-seconds, not hours as used in the current laboratory work. In order to address this issue, aside from a more powerful x-ray source and improved detector, it is also important to explore innovative data acquisition and corresponding imaging processing methods to reduce data acquisition time.

Fourth, when x-ray phase contrast imaging is used, it often involves a different requirement on the spatial coherence of the x-ray beams compared with standard x-ray imaging. When a spatially coherent x-ray wave is scattered by a granular structure inside the image object, the coherence will be diminished. As a result, the SNR of the phase contrast mechanism drops, and may even be completely lost. This is in stark contrast with the absorption contrast mechanism which is much more independent of the structure of the image object. Therefore, the phase contrast mechanism should perhaps be combined with conventional absorption contrast for medical diagnosis. Instead of using phase contrast as the sole contrast mechanism in medical diagnosis, a potential new paradigm in the future of x-ray imaging could be multi-contrast imaging, where the complementary information from each contrast mechanism is combined for use in medical diagnosis.

In light of the foregoing drawbacks, there remains a desire to provide systems and methods for generating x-ray phase contrast images that are readily attainable in the clinical setting without requiring specialized hardware systems or increased dose exposure to subjects.

SUMMARY OF THE INVENTION

The present invention overcomes the aforementioned drawbacks by providing systems and methods for generating an x-ray phase contrast image from conventional x-ray attenuation data without requiring special hardware modifications to currently available x-ray imaging systems.

It is an aspect of the invention to provide a method for producing an x-ray phase contrast image of an object from attenuation data acquired with an x-ray imaging system. Calibration data that includes a first calibration factor defining an energy dependence for a first component of x-ray attenuation and a second calibration factor defining an energy dependence for a second component of x-ray attenuation is provided. Then, using an x-ray imaging system, attenuation data is acquired from the object, the attenuation data containing attenuation information associated with x-rays having at least two different energies. From the attenuation data, a first spatial map indicative of the first component of x-ray attenuation and a second spatial map indicative of the second component of x-ray attenuation are produced. An x-ray phase contrast image is then produced using the calibration data and the first and second spatial maps.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
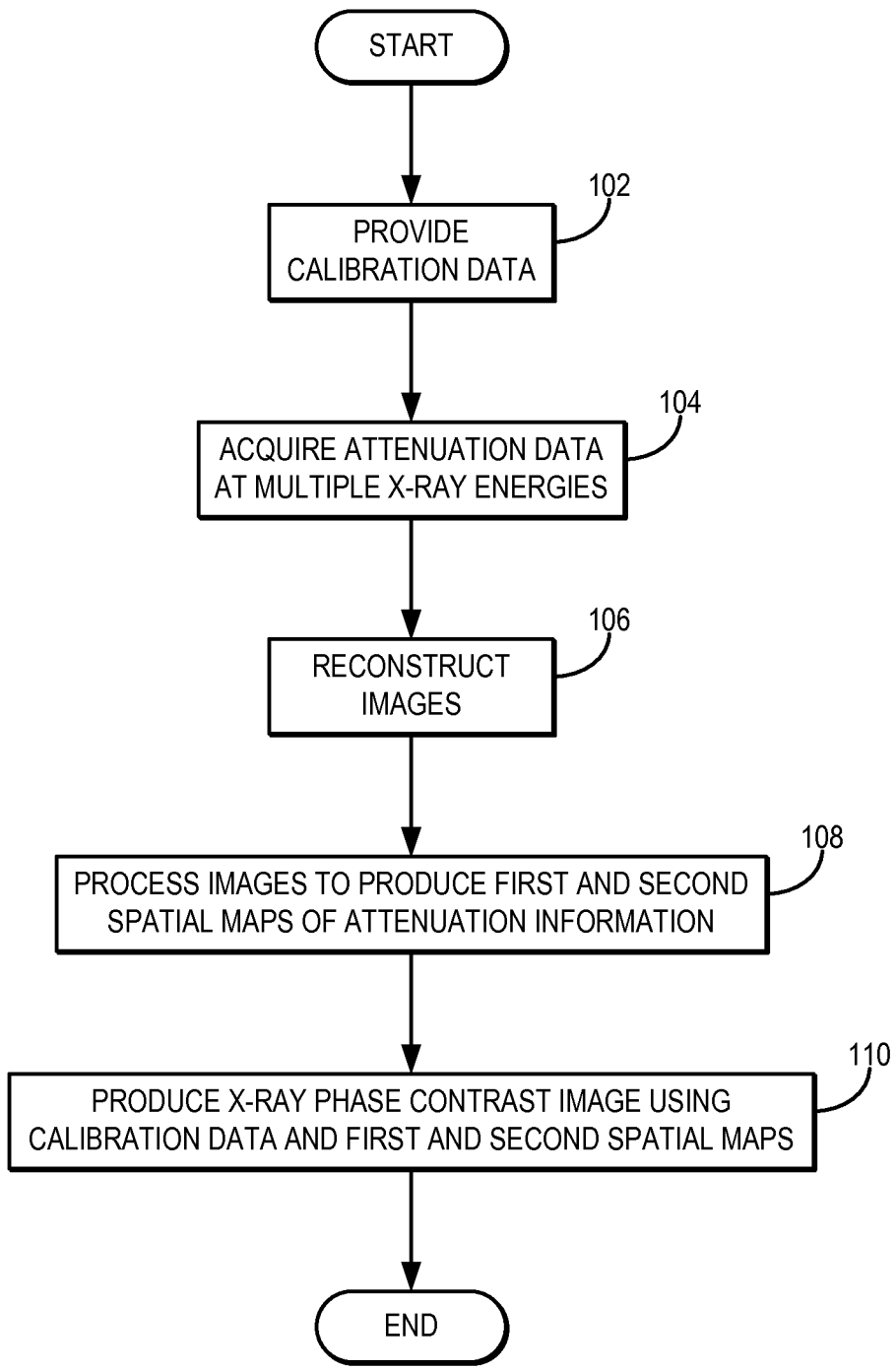
FIG. 1 is a flowchart setting forth the steps of a method for generating an x-ray phase contrast image from x-ray attenuation data.

Described here are systems and methods for generating x-ray phase contrast images using a standard x-ray tube-detector assembly, such as is used in a conventional x-ray absorption imaging data acquisition system. X-ray attenuation coefficients generated over a range of x-ray energies are used to compute the x-ray phase signal up to a calibration constant. This calibration constant is computed from provided calibration data, which may be obtained using a dedicated x-ray phase contrast imaging system to measure the decrement of the refractive index of a calibration phantom.

Note that the x-ray spectrum and the needed physical size of the calibration phantom can be much different from that of the final application, in which the object size can be as large as normal human subjects and the x-ray energy spectrum can be extended to the range in which high signal-to-noise ratio x-ray absorption signal can be generated.

The systems and methods described here are capable of generating x-ray phase contrast images using currently available x-ray imaging systems, such as those that acquire x-ray attenuation data. The systems and methods do not require spatial coherence of the x-ray source and, thus, are readily available for clinical use. The systems and method also do not require any modifications to currently the available dual-energy x-ray CT data acquisition methods and thus it is applicable to any dual energy CT acquisition systems.

Because of their wave-like properties, similar to the macroscopic phenomena observed in visible light, x-rays can experience reflection, refraction, diffraction, and interference at the interface of two different media. To describe these phenomena, a medium is often considered as containing homogeneous sub-regions with sharp boundaries, with each sub-region having its own macroscopic refractive index, n. By definition, a vacuum should not affect the wave and, thus, has a refractive index n=1. For visible light, the refractive index is often larger than one. For example, the refractive index of visible light in glass ranges from about 1.5 to 1.8. This large refractive index makes the observation of reflection and refraction of visible light easy in normal laboratory conditions. In contrast, for x-rays, the refractive index is much closer to unity, with the difference from one often being only about 0.1-10 parts per million ("PPM"). As a result, it is very difficult to directly observe x-ray refraction phenomena. In general, the refractive index for x-rays can be written as, $$n = 1 - \delta + i\beta \quad (1);$$

Where $\delta$ is the refractive index decrement, which is responsible for x-ray phase shifts, and $\beta$ is the imaginary part of the refractive index, which is responsible for x-ray attenuation. The refractive index is a dimensionless quantity and its imaginary part, $\beta$, is related to the conventional linear attenuation coefficient, $\mu$, as follows:

$$\mu = \frac{4\pi\beta}{\lambda}; \quad (2)$$

where $\lambda$ is the wavelength of the x-ray. Microscopically, the decrement and the imaginary part of the x-ray refractive index are given as, $$\delta = \frac{r_e \lambda^2 \rho_e}{2\pi}; \quad (3)$$

$$\beta = \frac{\lambda}{4\pi} \frac{\rho_e}{Z} (\sigma_{pe} + \sigma_C); \quad (4)$$

where $\rho_e$ is the electron density, $r_e = 2.818 \times 10^{-15}$ m is the classical radius of the electron, Z is the atomic number, $\sigma_{pe}$ is the photoelectric cross-section, and $\sigma_C$ is the Compton scattering cross-section. Because the photoelectric cross section decreases with energy, E, faster than $E^{-3}$, the imaginary part of the refractive index decreases with energy faster than $E^{-4}$. In contrast, the decrement of the refractive index only decreases with energy as $E^{-2}$.

The magnitude of the x-ray phase shift within a homogeneous medium is determined by the decrement of refractive index of the medium, $\delta$, and the thickness of the medium. An inhomogeneous medium can be treated as many homogeneous media with infinitesimal thickness and, thus, the total amount of x-ray phase shift, $\phi$, generated by an inhomogeneous object can be given by, $$\phi = \frac{2\pi}{\lambda} \int_l dl \delta(l) = r_e \lambda \int_l dl \rho_e(l); \quad (5)$$

where the integral is taken over the x-ray path length, l. Thus, the phase shift is uniquely determined by the distribution of electron density. This is in stark contrast to the imaginary part, $\beta$, and the related linear attenuation coefficient, which is dependent on both electron density and atomic number, as shown in Eqn. (4). The line integral of electron density expressed in Eqn. (5) is reminiscent of the attenuation of x-rays when they penetrate through a non-uniform medium. In the attenuation case, the logarithm of the ratio of entrance and exiting photon numbers gives a line integral of linear attenuation coefficient:

$$\ln \frac{N_0}{N} = \int_l dl \mu(l). \quad (6)$$

Based on Eqn. (5), and analogous to attenuation-based CT reconstruction, as long as the phase shift can be measured, tomographic reconstruction principles can be applied to the local distribution of electron density. To accomplish this, the phase shift is measured around the image object from many view angles, and the local electron density distribution is then reconstructed using an appropriate image reconstruction algorithm. This is the physical foundation of phase contrast CT; however, direct measurement of phase shift is often very difficult in practice.

Typically, the x-ray phase shifts need to be connected to other quantities that are easier to measure. The refraction angle, which is the angular deviation of the propagation direction of an exit wave from its incident propagation direction, is a measureable quantity to which phase shift can be directly related. Assuming that the x-ray wave propagates along the z-direction, the refraction phenomenon can be measured in the x-y plane, which is perpendicular to the wave propagation direction. The refraction angle, $\Theta$, is related to the phase shift as follows:

$$\Theta(x, y) = \frac{\lambda}{2\pi} \frac{\partial \phi(x, y)}{\partial x}. \quad (7)$$

This relationship has been used as a foundation in modern optics to investigate material properties. However, observation of this refraction effect for diagnostic x-rays is still very difficult as the refraction angle is on the order of microradians. In past years, investigators have tried many different schemes to measure the refraction angle or its variants.

It is important to note that the real and imaginary parts of the refractive index of a given material are not independent from each other. The real and imaginary parts of the refractive index collectively describe how the given material responds to a given x-ray wave when the wave propagates through the material. The complex refractive index is the response function between the external radiation field and the medium and, thus, would follow a rigid causal condition. For instance, before x-rays are delivered to the medium, the medium is not able to respond to the x-rays. Given this rigid causality condition, the so-called Kramer-Kronig Relationship ("KKR") can be derived without knowing any specific details of the interactions.

The KKR gives a specific relation between the real and imaginary parts of the complex refractive index. More explicitly, the KKR states that the real part of the complex refractive index can be calculated from the imaginary part of the same refractive index. In other words, the KKR states that the phase contrast signal, $\delta$, should be computable from the absorption contrast signal, $\mu$, provided that the attenuation coefficient can be measured or estimated at all of the x-ray energies. For a uniform medium, the KKR of the complex refractive index is given as, $$1 - \delta(E) = \frac{2}{\pi} \int_0^{+\infty} d\varepsilon \frac{\varepsilon \beta(\varepsilon)}{\varepsilon^2 - E^2} \quad (8)$$
$$= \frac{\hbar c}{\pi} \int_0^{+\infty} d\varepsilon \frac{\mu(\varepsilon)}{\varepsilon^2 - E^2};$$

$$\mu(E) = -\frac{4E^2}{\pi \hbar c} \int_0^{+\infty} d\varepsilon \frac{1 - \delta(\varepsilon)}{\varepsilon^2 - E^2}; \quad (9)$$

where $\hbar$ is the reduced Planck constant and c is the speed of light in vacuum. The above relations can be generalized to a non-uniform medium as, $$1 - \delta(r, E) = \frac{2}{\pi} \int_0^{+\infty} d\varepsilon \frac{\varepsilon \beta(r, \varepsilon)}{\varepsilon^2 - E^2} \quad (10)$$
$$= \frac{\hbar c}{\pi} \int_0^{+\infty} d\varepsilon \frac{\mu(r, \varepsilon)}{\varepsilon^2 - E^2};$$

$$\mu(r, E) = -\frac{4E^2}{\pi \hbar c} \int_0^{+\infty} d\varepsilon \frac{1 - \delta(r, \varepsilon)}{\varepsilon^2 - E^2}; \quad (11)$$

where r denotes a spatial point in the non-uniform medium (e.g., the image object). The above relations dictate that the phase contrast image, $\delta(r,E)$, of an image object can be computed from the corresponding attenuation image, $\mu(r,E)$, provided that the attenuation coefficients at all possible energies, $E \in [0, +\infty)$, are known for the image object. Vice versa, the attenuation image can be computed at a given energy from the corresponding phase contrast images, $\delta(r,E)$, provided that the phase contrast images are known for all possible energies.

Although the above fundamental relations provide a theoretical framework for computing phase contrast images from the attenuation images, it is impractical to perform the aforementioned integrals over energy due to two challenges. First, it is not possible to obtain attenuation images at an arbitrary energy. Second, the numerical integrations are unstable due to the singularities in the integral. The present invention is capable of overcoming these challenges and, thus, enables the generation of phase contrast images from absorption images without invoking the ad hoc numerical integrations.

When an x-ray imaging task is restricted to a specific x-ray energy range (e.g., 40 keV<E<140 keV, like in most diagnostic x-ray CT imaging), the imaginary part of the complex refractive index is primarily determined by the photoelectric and Compton scattering cross-sections, as shown in Eqn. (4). In this case, the attenuation coefficient, $\mu(r,E)$, can be decomposed into two terms with separable energy and spatial dependences:

$$\mu(r,E) = B_1(E)\mu_1(r) + B_2(E)\mu_2(r) \quad (12)$$

As will be described below, the attenuation coefficient can be decomposed into a number of different bases. In one example, the attenuation coefficient can be decomposed into x-ray attenuation effects associated with the photoelectric effect and x-ray attenuation effects associated with Compton scattering. In another example, the attenuation coefficient can be decomposed into x-ray attenuation components associated with a first and second material, such as water and bone. Substituting the decomposition of Eqn. (12) into Eqn. (10), the following equation can be derived to compute the phase contrast image:

$$1 - \delta(r, E) = \frac{\hbar c}{\pi} \int_0^{+\infty} d\varepsilon \frac{\mu(r, \varepsilon)}{\varepsilon^2 - E^2} \quad (13)$$
$$= \mu_1(r) B_1(E) + \mu_2(r) B_2(E);$$

where the two energy dependent factors, $B_1(E)$ and $B_2(E)$, are respectively defined as follows:

$$B_1(E) = \frac{\hbar c}{\pi} \int_0^{+\infty} d\varepsilon \frac{B_1(\varepsilon)}{\varepsilon^2 - E^2}; \quad (14)$$

$$B_2(E) = \frac{\hbar c}{\pi} \int_0^{+\infty} d\varepsilon \frac{B_2(\varepsilon)}{\varepsilon^2 - E^2}. \quad (15)$$

Note that the above factors are independent of materials. Therefore, one can use materials with known $\delta$ values and known components, $\mu_1$ and $\mu_2$, to determine $B_1(E)$ and $B_2(E)$ from Eqn. (13). This procedure for experimentally determining $B_1(E)$ and $B_2(E)$ can be referred to as a calibration procedure. Using the calibration factors, $B_1(E)$ and $B_2(E)$, determined from the calibration procedure, Eqn. (13) can be used to compute the desired phase contrast image, $\delta(r,E)$, at the calibration energy point, E, from the attenuation component maps, $\mu_1$ and $\mu_2$, which are obtained from a dual energy x-ray attenuation data using the data analysis described below.

Thus, in addition to obtaining the calibration data, the attenuation components, $\mu_1(r)$ and $\mu_2(r)$, for a given image object must also be obtained. This task can be accomplished using dual energy x-ray CT methods. In dual energy CT, attenuation properties of the image object are measured at two different polychromatic or monochromatic x-ray energy spectra. Then, dual energy data processing methods are used to generate the component image, $\mu_1(r)$, which in one example can be said to be in the basis of photoelectric effect, and the component image, $\mu_2(r)$, which in one example can be said to be in the basis of Compton effect.

Because the energy dependence factor in the photoelectric effect cross-section, $\sigma_{pe}$, and the energy dependence of the Compton scattering cross-section, $\sigma_C$, can be combined to generate the energy dependence factors for a pair of two different uniform mediums, such as water and bone, the aforementioned calibration procedure can be used to experimentally determine the corresponding calibration factors $B_1(E)$ and $B_2(E)$, for the specific attenuation components, $\mu_1$ and $\mu_2$, in this new pair of bases. After the calibration, the same Eqn. (13) can be used to compute the desired phase contrast image from the attenuation components, $\mu_1(r)$ and $\mu_2(r)$, of an unknown image object measured from the dual energy CT data acquisition and data analysis method.

Examples of methods that can be used to generate $\mu_1(r)$ and $\mu_2(r)$ include but are not limited to the following schemes: (1) fast kV switching technique can be used to acquire attenuation data at high and low tube potentials at two neighboring view angles; (2) acquiring low and high tube potential projection data from two independent source-detector assemblies; (3) acquiring low and high tube potential projection data in two consecutive data acquisitions using a single tube-detector assembly; (4) acquiring low and high tube potential projection data using a sandwich detector, in which two detector readout circuits are used to readout the measured projection data at two different energies in the first and second spatial portions, respectively, of the scintillation materials in the detector; and (5) acquiring data using a photon-counting detector, in which projection data can be read out at different energy bins.

Any of the above mentioned dual energy data acquisition methods can be used to acquire attenuation projection data to generate the spatial maps, $\mu_1(r)$ and $\mu_2(r)$, which can then be used in Eqn. (13) to compute the desired phase contrast image, $\delta(r,E)$, after the energy dependence factors are obtained from the calibration steps described below.

In order to obtain the energy calibration factors, $B_1(E)$ and $B_2(E)$, used in Eqn. (13), experimental methods can be used to measure $\delta(r,E)$, $\mu_1(r)$, and $\mu_2(r)$ for some known materials. By way of example, currently available x-ray phase contrast imaging systems, such as those that implement a Talbot interferometer, a Talbot-Lau interferometer, or a diffraction enhanced imaging ("DEI") method using a synchrotron radiation source, can be used to measure $\delta(r,E)$ and clinically available dual energy CT systems, such as those described above, can be used to measure $\mu_1(r)$ and $\mu_2(r)$. For instance, a calibration phantom having known materials can be scanned by both a phase contrast imaging system and a dual energy x-ray imaging system to derive the appropriate quantities for that phantom. The calibration phantom preferably contains two or more known materials, which can be imaging in the manner described above to obtain $\delta(r,E)$, $\mu_1(r)$, and $\mu_2(r)$, for those materials. By using a calibration phantom with two or more known materials, there will be two or more linear equations formed from Eqn. (13). A least squares fitting can then be used to estimate the desired calibration factors, $B_1(E)$ and $B_2(E)$, from Eqn. (13).

Referring now to FIG. 1, a flowchart setting forth the steps of an example of a method for generating a phase contrast image from data acquired with a conventional x-ray imaging system is illustrated. Calibration data is provided, as indicated at step 102. This calibration data can be obtained prior to the particular imaging task and stored for retrieval during the generation of the phase contrast image. An example method for producing calibration data is described below.

The object to be imaged, which may be an inanimate object or a living subject, is positioned in an x-ray imaging system, which is then operated to obtain attenuation data from the object at multiple different energies, as indicated at step 104. As described above, any number of different x-ray imaging systems and techniques can be used to acquire attenuation data at multiple x-ray energies. For instance, an x-ray imaging system capable of fast kV switching can be used to acquire attenuation data at high and low tube potentials at two neighboring view angles; a dual-source x-ray imaging system can be used; a single-source x-ray imaging system can be used to perform successive scans at different energies; an x-ray imaging system that incorporates a so-called "sandwich" detector can be used; or an x-ray imaging system that incorporates a photon-counting detector can be used.

From the acquired attenuation data, images of the object are reconstructed, as indicated at step 106. Using known techniques, spatial maps of $\mu_1$ and $\mu_2$ are then computed from the reconstructed images, as indicated at step 108. Together with the provided calibration data, the spatial maps of $\mu_1$ and $\mu_2$ are then used to generate a phase contrast image, as indicated at step 110. For instance, the calibration data may include the calibration factors, $B_1(E)$ and $B_2(E)$, such that Eqn. (13) can be used to compute the phase contrast image from the spatial maps of $\mu_1$ and $\mu_2$. By way of example, this phase contrast image may depict the electron density, $\rho_e$, in the imaged object.

Figure 2:
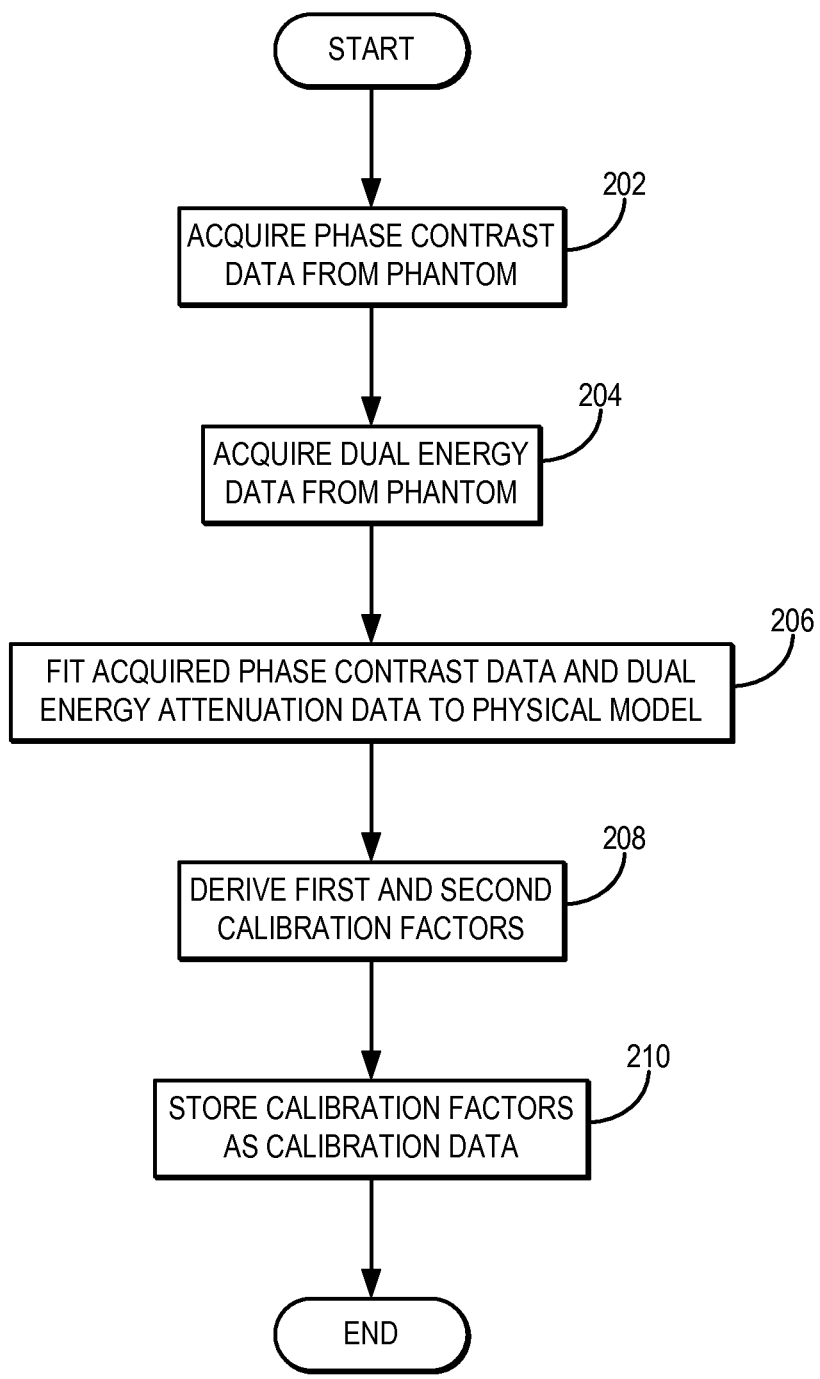
FIG. 2 is a flowchart setting forth the steps of a method for producing calibration data used in the method illustrated in FIG. 1.

Referring now to FIG. 2, a flowchart setting forth the steps of an example of a method for producing calibration data for use in generating an x-ray phase contrast image from attenuation data is illustrated. The method begins by acquiring x-ray phase contrast data from a calibration phantom, as indicated at step 202. This acquisition is performed using a dedicated x-ray phase contrast imaging system capable of acquiring x-ray phase contrast data, such as those systems mentioned above. Next, the same calibration phantom is scanned independently or together with another phantom or extension with a conventional x-ray imaging system to acquire dual-energy attenuation data, as indicated at step 204. As described above, any number of different imaging systems can be used to acquire dual-energy attenuation data.

The phase contrast and dual energy attenuation data are then fit to a physical model that described the photoelectric and Compton scattering effects of x-ray attenuation, as indicated at step 206. For example, the data can be fit to Eqn. (13). Using this fitting a first and second calibration factor are derived, as indicated at step 208. The first calibration factor, $B_1(E)$, defines an energy dependence for x-ray attenuation associated with photoelectric effects and the second calibration factor, $B_2(E)$, defines an energy dependence for x-ray attenuation associated with Compton scattering. The first and second calibration factors are then stored as the calibration data, as indicated at step 210.

The energy calibration factors, $B_1(E)$ and $B_2(E)$, for other basis materials, such as water and bone, can also be obtained. In this case, the attenuation component images, $\mu_1$ and $\mu_2$, are the corresponding components in a basis of the new pair of basis materials.

Figure 3A:
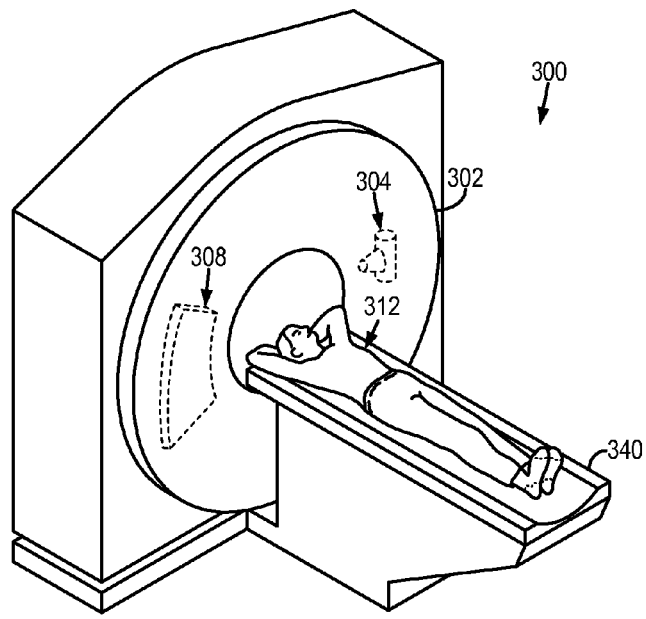
FIGS. 3A and 3B illustrate an example of an x-ray computed tomography imaging system.
Figure 3B:
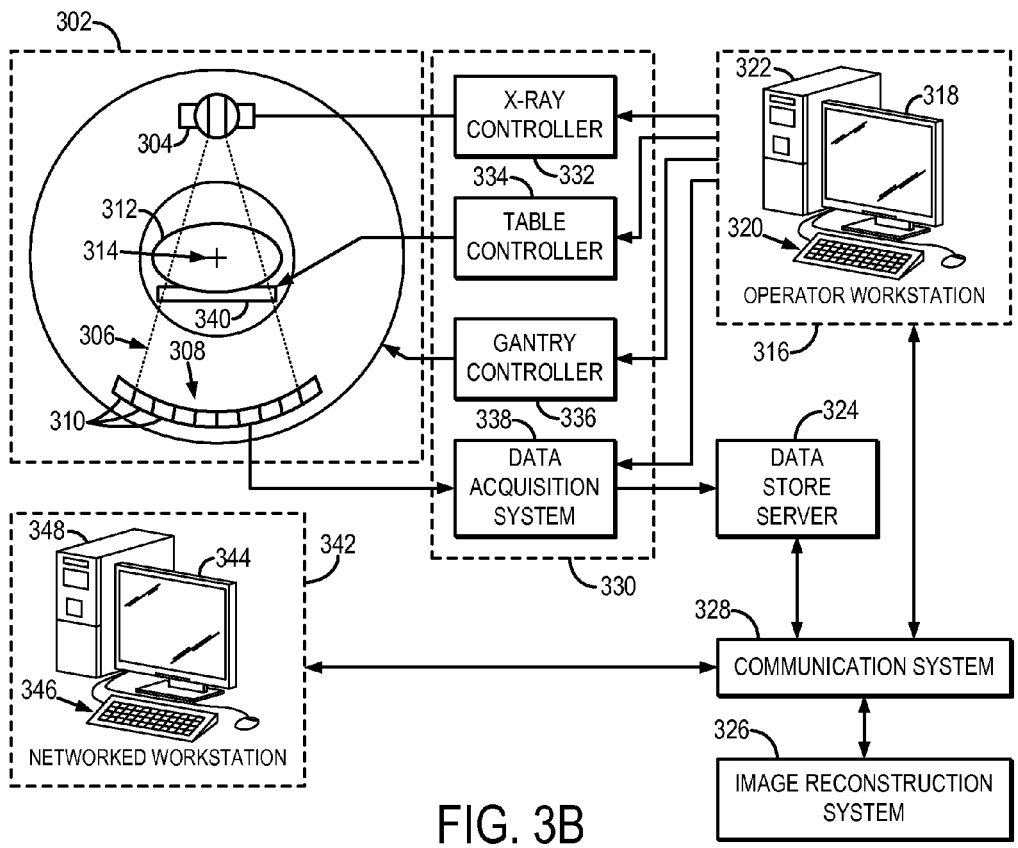

Referring particularly now to FIGS. 3A and 3B, an example of an x-ray computed tomography ("CT") imaging system 300 is illustrated. The CT system includes a gantry 302, to which at least one x-ray source 304 is coupled. The x-ray source 304 projects an x-ray beam 306, which may be a fan-beam or cone-beam of x-rays, towards a detector array 308 on the opposite side of the gantry 302. The detector array 308 includes a number of x-ray detector elements 310. Together, the x-ray detector elements 310 sense the projected x-rays 306 that pass through a subject 312, such as a medical patient or an object undergoing examination, that is positioned in the CT system 300. Each x-ray detector element 310 produces an electrical signal that may represent the intensity of an impinging x-ray beam and, hence, the attenuation of the beam as it passes through the subject 312. In some configurations, each x-ray detector 310 is capable of counting the number of x-ray photons that impinge upon the detector 310. During a scan to acquire x-ray projection data, the gantry 302 and the components mounted thereon rotate about a center of rotation 314 located within the CT system 300.

The CT system 300 also includes an operator workstation 316, which typically includes a display 318; one or more input devices 320, such as a keyboard and mouse; and a computer processor 322. The computer processor 322 may include a commercially available programmable machine running a commercially available operating system. The operator workstation 316 provides the operator interface that enables scanning control parameters to be entered into the CT system 300. In general, the operator workstation 316 is in communication with a data store server 324 and an image reconstruction system 326. By way of example, the operator workstation 316, data store sever 324, and image reconstruction system 326 may be connected via a communication system 328, which may include any suitable network connection, whether wired, wireless, or a combination of both. As an example, the communication system 328 may include both proprietary or dedicated networks, as well as open networks, such as the internet.

The operator workstation 316 is also in communication with a control system 330 that controls operation of the CT system 300. The control system 330 generally includes an x-ray controller 332, a table controller 334, a gantry controller 336, and a data acquisition system 338. The x-ray controller 332 provides power and timing signals to the x-ray source 304 and the gantry controller 336 controls the rotational speed and position of the gantry 302. The table controller 334 controls a table 340 to position the subject 312 in the gantry 302 of the CT system 300.

The DAS 338 samples data from the detector elements 310 and converts the data to digital signals for subsequent processing. For instance, digitized x-ray data is communicated from the DAS 338 to the data store server 324. The image reconstruction system 326 then retrieves the x-ray data from the data store server 324 and reconstructs an image therefrom. The image reconstruction system 326 may include a commercially available computer processor, or may be a highly parallel computer architecture, such as a system that includes multiple-core processors and massively parallel, high-density computing devices. Optionally, image reconstruction can also be performed on the processor 322 in the operator workstation 316. Reconstructed images can then be communicated back to the data store server 324 for storage or to the operator workstation 316 to be displayed to the operator or clinician.

The CT system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 316, or in a different facility, such as a different healthcare institution or clinic.

The networked workstation 342, whether within the same facility or in a different facility as the operator workstation 316, may gain remote access to the data store server 324 and/or the image reconstruction system 326 via the communication system 328. Accordingly, multiple networked workstations 342 may have access to the data store server 324 and/or image reconstruction system 326. In this manner, x-ray data, reconstructed images, or other data may be exchanged between the data store server 324, the image reconstruction system 326, and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

In some configurations, the CT system 300 may be a dual-source system that includes two x-ray sources and two x-detector arrays. In some configurations, as described above, the CT system 300 may be configured to rapidly switch the x-ray source 304 between a high and a low tube potential such that adjacent pairs of view angles are acquired at two different x-ray energies. In some configurations, the CT system 300 may include a detector array 308 that includes two different detector portions capable of separately discriminating two different x-ray energies. In some configurations, the CT system 300 may include a detector array 308 that is a photon-counting detector capable of acquiring data and separating it into distinct energy bins.

Figure 4:
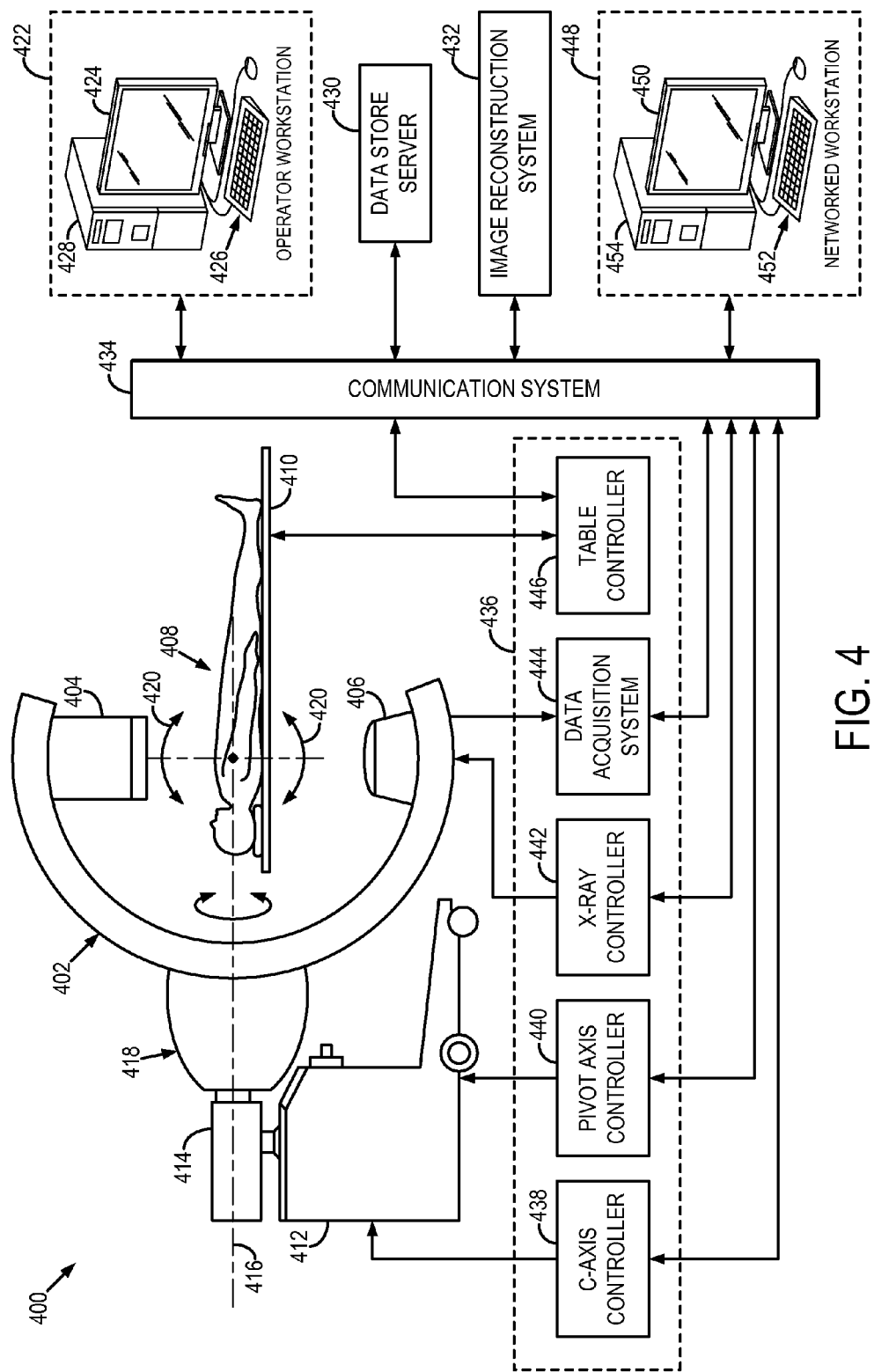
FIG. 4 illustrates an example of a C-arm x-ray imaging system.

Referring particularly to FIG. 4, an example of a so-called "C-arm" x-ray imaging system 400 is illustrated. Such an imaging system is generally designed for use in connection with interventional procedures. The C-arm x-ray imaging system 400 includes a gantry 402 having a C-arm to which an x-ray source assembly 404 is coupled on one end and an x-ray detector array assembly 406 is coupled at its other end. The gantry 402 enables the x-ray source assembly 404 and detector array assembly 406 to be oriented in different positions and angles around a subject 408, such as a medical patient or an object undergoing examination, that is positioned on a table 410. When the subject 408 is a medical patient, this configuration enables a physician access to the subject 408.

The x-ray source assembly 404 includes at least one x-ray source that projects an x-ray beam, which may be a fan-beam or cone-beam of x-rays, towards the x-ray detector array assembly 406 on the opposite side of the gantry 402. The x-ray detector array assembly 406 includes at least one x-ray detector, which may include a number of x-ray detector elements. Examples of x-ray detectors that may be included in the x-ray detector array assembly 406 include flat panel detectors, such as so-called "small flat panel" detectors, in which the detector array panel is around 20×20 centimeters in size. Such a detector panel allows the coverage of a field-of-view of around twelve centimeters.

Together, the x-ray detector elements in the one or more x-ray detectors housed in the x-ray detector array assembly 406 sense the projected x-rays that pass through a subject 408. Each x-ray detector element produces an electrical signal that may represent the intensity of an impinging x-ray beam and, thus, the attenuation of the x-ray beam as it passes through the subject 408. In some configurations, each x-ray detector element is capable of counting the number of x-ray photons that impinge upon the detector. During a scan to acquire x-ray projection data, the gantry 402 and the components mounted thereon rotate about an isocenter of the C-arm x-ray imaging system 400.

The gantry 402 includes a support base 412. A support arm 414 is rotatably fastened to the support base 412 for rotation about a horizontal pivot axis 416. The pivot axis 416 is aligned with the centerline of the table 410 and the support arm 414 extends radially outward from the pivot axis 416 to support a C-arm drive assembly 418 on its outer end. The C-arm gantry 402 is slidably fastened to the drive assembly 418 and is coupled to a drive motor (not shown) that slides the C-arm gantry 402 to revolve it about a C-axis, as indicated by arrows 420. The pivot axis 416 and C-axis are orthogonal and intersect each other at the isocenter of the C-arm x-ray imaging system 400, which is indicated by the black circle and is located above the table 410.

The x-ray source assembly 404 and x-ray detector array assembly 406 extend radially inward to the pivot axis 416 such that the center ray of this x-ray beam passes through the system isocenter. The center ray of the x-ray beam can thus be rotated about the system isocenter around either the pivot axis 416, the C-axis, or both during the acquisition of x-ray attenuation data from a subject 408 placed on the table 410. During a scan, the x-ray source and detector array are rotated about the system isocenter to acquire x-ray attenuation projection data from different angles. By way of example, the detector array is able to acquire thirty projections, or views, per second.

The C-arm x-ray imaging system 400 also includes an operator workstation 422, which typically includes a display 424; one or more input devices 426, such as a keyboard and mouse; and a computer processor 428. The computer processor 428 may include a commercially available programmable machine running a commercially available operating system. The operator workstation 422 provides the operator interface that enables scanning control parameters to be entered into the C-arm x-ray imaging system 400. In general, the operator workstation 422 is in communication with a data store server 430 and an image reconstruction system 432. By way of example, the operator workstation 422, data store sever 430, and image reconstruction system 432 may be connected via a communication system 434, which may include any suitable network connection, whether wired, wireless, or a combination of both. As an example, the communication system 434 may include both proprietary or dedicated networks, as well as open networks, such as the internet.

The operator workstation 422 is also in communication with a control system 436 that controls operation of the C-arm x-ray imaging system 400. The control system 436 generally includes a C-axis controller 438, a pivot axis controller 440, an x-ray controller 442, a data acquisition system ("DAS") 444, and a table controller 446. The x-ray controller 442 provides power and timing signals to the x-ray source assembly 404, and the table controller 446 is operable to move the table 410 to different positions and orientations within the C-arm x-ray imaging system 400.

The rotation of the gantry 402 to which the x-ray source assembly 404 and the x-ray detector array assembly 406 are coupled is controlled by the C-axis controller 438 and the pivot axis controller 440, which respectively control the rotation of the gantry 402 about the C-axis and the pivot axis 416. In response to motion commands from the operator workstation 422, the C-axis controller 438 and the pivot axis controller 440 provide power to motors in the C-arm x-ray imaging system 400 that produce the rotations about the C-axis and the pivot axis 416, respectively. For example, a program executed by the operator workstation 422 generates motion commands to the C-axis controller 438 and pivot axis controller 440 to move the gantry 402, and thereby the x-ray source assembly 404 and x-ray detector array assembly 406, in a prescribed scan path.

The DAS 444 samples data from the one or more x-ray detectors in the x-ray detector array assembly 406 and converts the data to digital signals for subsequent processing. For instance, digitized x-ray data is communicated from the DAS 444 to the data store server 430. The image reconstruction system 432 then retrieves the x-ray data from the data store server 430 and reconstructs an image therefrom. The image reconstruction system 430 may include a commercially available computer processor, or may be a highly parallel computer architecture, such as a system that includes multiple-core processors and massively parallel, high-density computing devices. Optionally, image reconstruction can also be performed on the processor 428 in the operator workstation 422. Reconstructed images can then be communicated back to the data store server 430 for storage or to the operator workstation 422 to be displayed to the operator or clinician.

The C-arm x-ray imaging system 400 may also include one or more networked workstations 448. By way of example, a networked workstation 448 may include a display 450; one or more input devices 452, such as a keyboard and mouse; and a processor 454. The networked workstation 448 may be located within the same facility as the operator workstation 422, or in a different facility, such as a different healthcare institution or clinic.

The networked workstation 448, whether within the same facility or in a different facility as the operator workstation 422, may gain remote access to the data store server 430, the image reconstruction system 432, or both via the communication system 434. Accordingly, multiple networked workstations 448 may have access to the data store server 430, the image reconstruction system 432, or both. In this manner, x-ray data, reconstructed images, or other data may be exchanged between the data store server 430, the image reconstruction system 432, and the networked workstations 448, such that the data or images may be remotely processed by the networked workstation 448. This data may be exchanged in any suitable format, such as in accordance with the transmission control protocol ("TCP"), the internet protocol ("IP"), or other known or suitable protocols.

Thus, systems and methods for generating x-ray phase contrast images from conventional attenuation data have been provided. Using a calibration procedure that uses a true differential phase contrast data, a conventional dual energy CT data acquisition system is readily turned into a x-ray phase contrast CT imaging system to obtain x-ray phase contrast images. The differential phase contrast data acquisition system does not need to have large field of view for clinical use since it is only used in calibration process. The differential phase contrast data acquisition system also does not need to operate at really high x-ray energy levels. The generated x-ray phase contrast image has simple energy dependence $E^{-2}$; therefore, as long as the x-ray phase contrast image is obtained at one energy, it can be readily scaled to obtain an x-ray phase contrast image at other energies. Advantageously, the systems and methods of the present invention do not require any special hardware modifications to current dual energy CT systems to achieve the x-ray phase contrast imaging described here.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an x-ray phase contrast image of an object from attenuation data acquired with an x-ray imaging system, the steps of the method comprising:
a) providing calibration data that includes a first calibration factor defining an energy dependence for a first component of x-ray attenuation and a second calibration factor defining an energy dependence for a second component of x-ray attenuation;
b) acquiring attenuation data from the object using an x-ray imaging system, the attenuation data containing attenuation information associated with x-rays having at least two different energies;
c) producing from the attenuation data, a first spatial map indicative of the first component of x-ray attenuation and a second spatial map indicative of the second component of x-ray attenuation; and
d) producing an x-ray phase contrast image using the calibration data and the first and second spatial maps.

2. The method as recited in claim 1, wherein step d) includes weighting the first spatial map with the first calibration factor, weighting the second spatial map with the second calibration factor, and combining the weighted first and second spatial maps.

3. The method as recited in claim 1, wherein step c) includes reconstructing a first image at a first energy level and a second image at a second energy level and processing the first and second images to produce the first and second spatial maps.

4. The method as recited in claim 1, wherein step a) includes acquiring phase contrast data from a calibration phantom using an x-ray phase contrast imaging system, acquiring dual energy attenuation data from the calibration phantom using an x-ray imaging system, and fitting the phase contrast data and the dual energy attenuation data to a physical model to derive the first and second calibration factors.

5. The method as recited in claim 4, wherein the physical model in step a) models a complex refractive index of x-rays.

6. The method as recited in claim 1, wherein step b) includes acquiring attenuation data associated with two different x-ray energies.

7. The method as recited in claim 6, wherein step b) includes acquiring the attenuation data using an x-ray imaging system configured to switch between a high tube potential and a low tube potential when acquiring data along adjacent view angles.

8. The method as recited in claim 6, wherein step b) includes acquiring the attenuation data using a dual-source x-ray imaging system.

9. The method as recited in claim 6, wherein step b) includes performing a first scan to acquire attenuation data at the first x-ray energy and performing a second scan to acquire attenuation data at the second x-ray energy.

10. The method as recited in claim 6, wherein step b) includes acquiring the attenuation data using an x-ray imaging system that includes a sandwich detector that discriminates attenuation data at a first energy detected in a first portion of the detector from attenuation data at a second energy in a second portion of the detector.

11. The method as recited in claim 6, wherein step b) includes acquiring the attenuation data using an x-ray imaging system that includes a photon-counting detector capable of reading out data at different energy bins.

12. The method as recited in claim 6, wherein the x-ray imaging system is at least one of a C-arm imaging system and a computed tomography imaging system.

13. The method as recited in claim 1, further comprising producing another x-ray phase contrast image indicative of an x-ray phase contrast at a different energy level than the x-ray phase contrast image produced in step d) by scaling the x-ray phase contrast image produced in step d) by a scaling factor.

14. The method as recited in claim 1, wherein the first component of x-ray attenuation quantifies x-ray attenuation associated with photoelectric effects and the second component of x-ray attenuation quantifies x-ray attenuation associated with Compton scattering.

15. The method as recited in claim 1, wherein the first component of x-ray attenuation quantifies x-ray attenuation associated with a first material and the second component of x-ray attenuation quantifies x-ray attenuation associated with a second material.

16. The method as recited in claim 15, wherein the first material is water and the second material is bone.

17. The method as recited in claim 15, wherein step a) includes:
- acquiring phase contrast data from a calibration phantom using an x-ray phase contrast imaging system, wherein the calibration phantom contains materials with similar attenuation properties as the first and second materials;
- acquiring dual energy attenuation data from the calibration phantom using an x-ray imaging system;
- and fitting the phase contrast data and the dual energy attenuation data to a physical model to derive the first and second calibration factors.

18. The method as recited in claim 17, wherein the first material is water and the second material is bone.

* * * * *